United States Patent [19]

Bryant et al.

[11] Patent Number: 5,552,433

[45] Date of Patent: Sep. 3, 1996

[54] METHOD FOR LOWERING SERUM CHOLESTEROL

[75] Inventors: Henry U. Bryant; Timothy A. Grese, both of Indianapolis, Ind.

[73] Assignee: Eli Lilly and Company, Indianapolis, Ind.

[21] Appl. No.: 515,418

[22] Filed: Aug. 15, 1995

Related U.S. Application Data

[62] Division of Ser. No. 138,823, Oct. 15, 1993, Pat. No. 5,482,950.

[51] Int. Cl.$^6$ .................................................. A61K 31/38
[52] U.S. Cl. ............................................................ 514/443
[58] Field of Search ............................................. 514/443

[56] References Cited

U.S. PATENT DOCUMENTS

| | | | |
|---|---|---|---|
| 4,133,814 | 1/1979 | Jones et al. | 260/326.55 A |
| 4,380,635 | 4/1983 | Peters | 546/202 |
| 4,418,068 | 11/1983 | Jones | 424/267 |

FOREIGN PATENT DOCUMENTS

| | | |
|---|---|---|
| WO93/10113 | 5/1993 | WIPO . |
| WO93/1074 | 6/1993 | WIPO . |

OTHER PUBLICATIONS

Draper et al., "Effects of Raloxifene (LY139481 HCl) on Biochemical Markers of Bone and Lipid Metabolism in Healthy Postmenopausal Women", Hong Kong, Fourth Int'l Symp. on Osteoporosis, Mar. 29, 1993.

Bryant et al., "Protection from Bone Loss and Lowering of Serum Cholesterol in the Absence of Uterine Stimulation in Ovariectomized Rats", Am Soc. Bone & Min. Res., Tampa, Sep. 18–22, 1993.

Bryant et al., "Raloxifene is a Tissue Specific Estrogen Agonist", Am Soc. Bone & Min. Res., Tampa, Sep. 18–22, 1993.

Frolik et al., "In Vivo and In Vitro Metabolism of Raloxifene", Am. Soc. Bone & Min. Res., Tampa, Sep. 18–22, 1993.

Glasebrook et al., "Multiple Binding Sites for the Anti–estrogen Raloxifene", Am Soc. Bone & Min. Res., Tampa, Sep. 18–22, 1993.

Hock et al., "Combination of Raloxifene and Human Parathyoid Hormone 1–34; Increased Femur Bone Mass in Young Ovariectomized (OVX) Rats", Am. Soc. Bone & Min. Res., Tampa, Sep. 18–22, 1993.

Sato et al., "DEXA Analysis of Raloxifene Effects on the Bones From Ovariectomized Rats", Am. Soc. for Bone and Min. Res., Tampa, Sep. 18–22, 1993.

Yang et al., "Raloxifene an Anti–Estrogen, Simulates the Effects of Estrogen in Inhibiting Bone Resorption Through Regulating TGFB–3 Expression in Bone"; .Am Soc. for Bone and Min. Res., Tampa, Sep. 18–22, 1993.

*Primary Examiner*—Marianne M. Cintins
*Assistant Examiner*—Phyllis G. Spivack
*Attorney, Agent, or Firm*—James J. Sales

[57] ABSTRACT

A method of lowering serum cholesterol levels is disclosed comprising administering to a human in need of treatment an effective amount of a compound having the formula

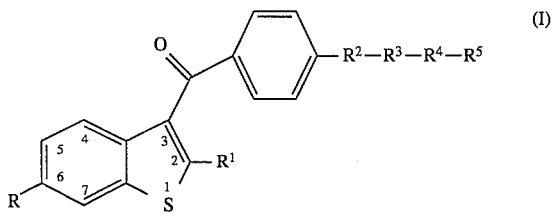

wherein R is herein defined;

$R^1$ is halo, $C_1$–$C_6$ alkyl, $C_1$–$C_7$ alkyl substituted with $C_1$–$C_6$ alkyl, substituted or unsubstituted $C_3$–$C_7$ cycloalkyl, or substituted or unsubstituted $C_3$–$C_7$ cycloalkenyl;

$R^2$ is O or $CH_2$;

$R^3$ is $CH_2$ or $(CH_2)_2$;

$R^4$ is

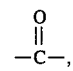

$CH_2$, or a bond; and $R^5$ is amino, or a pharmaceutically acceptable salt or solvate thereof.

9 Claims, No Drawings

METHOD FOR LOWERING SERUM CHOLESTEROL

This application is a division, of application Ser. No. 08/138,823 filed Oct. 15, 1993, now U.S. Pat. No. 5,482,950.

BACKGROUND OF THE INVENTION

All mammalian cells require cholesterol as a structural component of their cell membranes and for non-sterol end products. Cholesterol is also required for steroid hormone synthesis. The very property, however, that makes cholesterol useful in the cell membranes, its insolubility in water, also makes it potentially lethal. When cholesterol accumulates in the wrong place, for example within the wall of an artery, it cannot be readily mobilized and its presence leads to the development of an atherosclerotic plaque. Elevated concentrations of serum cholesterol associated with low density lipoproteins have been demonstrated to be a major contributing factor in the development and progression of atherosclerosis.

In mammals, serum lipoprotein is composed of cholesterol together with cholesteryl esters, triglycerides, phospholipids and apoproteins. Serum or plasma lipoprotein is comprised of several fractions. The major fractions or classes of plasma lipoproteins are very low density lipoprotein (VLDL), low density lipoprotein (LDL), intermediate density lipoprotein (IDL), and high density lipoprotein (HDL). These classes differ from one another in size, density and in the relative proportions of triglycerides and cholesteryl esters in the core, and in the nature of the apoproteins on the surface.

In mammals, serum cholesterol is derived from exogenous dietary sources as well as through endogenous synthesis. Endogenous synthesis of cholesterol involves a complex set of enzyme-catalyzed reactions and regulatory mechanisms generally termed the mevalonate pathway. Cells face a complex problem in regulating mevalonate synthesis because cholesterol, the bulk end product of mevalonate metabolism, is derived from plasma low density lipoprotein which enters the cell by receptor-mediated endocytosis, as well as from synthesis within the cell. Each cell must balance these external and internal sources so as to sustain mevalonate synthesis while avoiding sterol over accumulation. This balance is achieved through feedback regulation of at least two sequential enzymes in mevalonate synthesis, 3-hydroxy-3-methylglutaryl coenzyme A (HMG-CoA) synthase and HMG-CoA reductase and also of LDL receptors. In the absence of LDL, mammalian cells maintain high activities of the two enzymes, thereby synthesizing mevalonate for production of cholesterol as well as the non-sterol products. When LDL is present, from exogenous sources, HMG-CoA synthase and reductase activity is repressed and the cells produce smaller amounts of mevalonate for the non-sterol end products.

Abundant evidence indicates that treatment of hyperlipoproteinemia will diminish or prevent atherosclerotic complications. In addition to a diet that maintains a normal body weight and minimizes concentrations of lipids in plasma, therapeutic strategies include elimination of factors that exacerbate hyperlipoproteinemia and the administration of therapeutic agents that lower plasma concentrations of lipoproteins, either by diminishing the production of lipoproteins or by enhancing the efficiency of their removal from plasma.

The most promising class of drugs currently available for the treatment of hypercholesterolemia act by inhibiting HMG-CoA reductase, the rate-limiting enzyme of endogenous cholesterol synthesis. Drugs of this class competitively inhibit the activity of the enzyme. Eventually, this lowers the endogenous synthesis of cholesterol and, by normal homeostatic mechanisms, plasma cholesterol is taken up by LDL receptors to restore the intracellular cholesterol balance.

Relative to other cells in the body, liver cells play a critical role in maintaining serum cholesterol homeostasis by both releasing precursors of LDL and through receptor mediated LDL uptake from the serum. In both man and animal models an inverse correlation appears to exist between liver LDL receptors and LDL-associated serum cholesterol levels. In general, higher hepatocyte receptor numbers result in lower LDL-associated serum cholesterol levels. Cholesterol released into hepatocytes can be stored as cholesterol esters, converted into bile acids and released into the bile duct, or enter into an oxycholesterol pool. It is this oxycholesterol pool that is believed to be involved in end product repression of both the genes of the LDL receptor and enzymes involved in the cholesterol synthetic pathway.

Transcription of the LDL receptor gene is known to be repressed when cells have an excess supply of cholesterol, probably in the form of oxycholesterol. A DNA sequence in the LDL receptor promoter region, known as the sterol response element, appears to confer this sterol end product repression. This element has been extensively studied (Brown, Goldstein and Russell, U.S. Pat. Nos. 4,745,060 and 4,935,363) and appears to consist of a 16 base pair sequence that occurs 5' of the LDL receptor coding region. The sterol response element can be inserted into genes that normally do not respond to cholesterol, conferring sterol end product repression on the chimeric gene. The exact mechanism of this repression is not understood. There is, however, abundant evidence that polar intermediates in cholesterol biosynthesis and naturally occurring as well as synthetic hydroxysterols repress genes containing the sterol response element.

It has been suggested that a hydroxycholesterol binding protein serves as a receptor. When the receptor is bound to an oxysterol it acts on the sterol response element to control transcription through a mechanism that is similar to the action of members of the steroid hormone receptor super gene family.

In populations where coronary heart disease is a major health problem, the incidence of the disease is markedly lower in women than in men. This is particularly true in younger age groups, such as men and women between 35 and 44 years of age.

Generally, plasma lipoprotein metabolism is influenced by the circulating concentrations of gonadal steroids. Changes in serum estrogen and androgen concentrations, resulting from alterations in gonadal status or from the administration of exogenous gonadal steroids are associated with changes in serum lipoprotein levels. The changes effected by estrogens and androgens generally support the proposition that sex differences in lipoproteins are due to hormonal differences between men and women.

The generally accepted relationship between gonadal steroids and plasma lipoproteins is that androgens lower HDL concentrations and increase LDL, thus contributing to the low HDL and high LDL levels observed in men when compared to women. Estrogens are held to have opposite effects on lipoproteins; that is, HDL is raised and LDL is lowered. These sex steroid-induced differences in lipoprotein concentrations are thought to contribute to the lower incidence of cardiovascular disease in women compared to men. After the menopause, the protective effect of estrogens in women is lost and the incidence of cardiovascular disease increases towards the male levels. Postmenopausal women who take estrogens generally have lower rates of cardiovascular disease than women of a similar age who do not. Estrogen, particularly when taken orally, lowers plasma levels of LDL and raises those of HDL.

The mechanisms by which estrogen lowers levels of LDL and raises those of HDL are not known. In general, changes in the plasma concentration of a lipoprotein result from changes in the rate of its synthesis or the rate of its catabolism. For example, estrogen may lower LDL levels by increasing the clearance of LDL from plasma, since estrogen increases the number of hepatic LDL receptors in animals.

Although estrogens have beneficial effects on serum LDL, given even at very low levels, long-term estrogen therapy has been implicated in a variety of disorders, including an increase in the risk of uterine cancer and possibly breast cancer, causing many women to avoid this treatment. Recently suggested therapeutic regimens, which seek to lessen the cancer risk, such as administering combinations of progestogen and estrogen, cause the patient to experience regular bleeding, which is unacceptable to most older women. Furthermore, combining progesterone with estrogen seems to blunt the serum cholesterol lowering effects of estrogen. Concerns over the significant undesirable effects associated with estrogen therapy, support the need to develop alternative therapies for hypercholesterolemia that generates the desirable effects on serum LDL but does not cause undesirable effects.

Attempts to fill this need by the use of compounds commonly known as antiestrogens, which interact with the estrogen receptor and/or bind what has been termed the antiestrogen binding site (AEBS), have had limited success, perhaps due to the fact that these compounds generally display a mixed agonist/antagonist effect. That is, although these compounds can antagonize estrogen interaction with the receptor, the compounds themselves may cause estrogenic responses in those tissues having estrogen receptors such as the uterus. Therefore, some antiestrogens, such as Tamoxifen, are subject to the same adverse effects associated with estrogen therapy.

The current invention provides methods for lowering serum LDL without the associated adverse effects of estrogen therapy, and thus serve as an effective and acceptable treatment for hypercholesterolemia.

SUMMARY OF THE INVENTION

This invention provides methods for lowering serum cholesterol levels, comprising administering to a human in need of treatment an effective amount of a compound of formula I

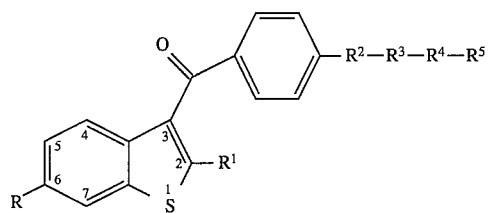

wherein R is hydrogen; hydroxy; $C_1$–$C_6$ alkoxy; a group of the formula —O—C(O)—$R^a$, wherein $R^a$ is hydrogen, $C_1$–$C_6$ alkyl optionally substituted with amino, halo, carbonyl, $C_1$–$C_6$ alkoxycarbonyl, $C_1$–$C_7$ alkanoyloxy, carbamoyl and/or aryl; or $R^a$ is $C_1$–$C_6$ alkenyl optionally substituted with aryl; or $R^a$ is a $C_3$–$C_7$ cycloalkyl; or $R^a$ is aryl optionally substituted with hydroxy, $C_1$–$C_6$ alkyl, $C_1$–$C_6$ alkoxy, and/or halo; or $R^a$ is —O-aryl, said aryl optionally substituted with hydroxy $C_1$–$C_6$ alkyl, $C_1$–$C_6$ alkoxy, and/or halo, or R is a group of the formula —O—$SO_2$—$R^b$ wherein $R^b$ may be $C_1$–$C_6$ alkyl or aryl optionally substituted with $C_1$–$C_6$ alkyl;

or R is carbamoyloxy wherein the nitrogen may be substituted once or twice with $C_1$–$C_6$ alkyl;

or R is a group of the formula —O—C(O)$R^c$—O—($C_1$–$C_6$ alkyl) wherein $R^c$ is a bond or $C_1$–$C_6$ alkanediyl;

$R^1$ is halo, $C_1$–$C_6$ alkyl, $C_1$–$C_7$ alkyl substituted with $C_1$–$C_6$ alkyl, substituted or unsubstituted $C_3$–$C_7$ cycloalkyl, or substituted or unsubstituted $C_3$–$C_7$ cycloalkenyl;

$R^2$ is O or $CH_2$;

$R^3$ is $CH_2$ or $(CH_2)_2$;

$R^4$ is

$CH_2$, or a bond; and $R^5$ is amino, optionally substituted once or twice with $C_1$–$C_6$ alkyl; or an N-heterocyclic ring which optionally has another hetero atom selected from N, O, or S in said ring; or a pharmaceutically acceptable salt or solvate thereof.

DETAILED DESCRIPTION OF THE INVENTION

The general chemical terms used in the description of a compound of formula I have their usual meanings. For example, the term "alkyl" by itself or as part of another substitutent means a straight or branched chain alkyl radical having the stated number of carbon atoms such as methyl, ethyl, propyl, and isopropyl and higher homologues and isomers where indicated.

The term "alkoxy" means an alkyl group having the stated number of carbon atoms linked by an oxygen atom, such as methoxy, ethoxy, propoxy, butoxy, pentyloxy, and hexyloxy and also includes branched chain structures such as, for example, isopropoxy and isobutoxy.

The term "$C_1$–$C_7$-alkanoyloxy" means a group —O—C(O)—$R^a$ where $R^a$ is hydrogen, or $C_1$–$C_6$ alkyl and includes formyloxy, acetoxy, propanoyloxy, butanoyloxy, pentanoyloxy, hexanoyloxy, and the like and also includes branched chain isomers such as, for example, 2,2-dimethylpropanoyloxy, and 3,3-dimethylbutanoyloxy.

When R is a group of the formula —O—C(O)—$R^c$—O—($C_1$–$C_6$ alkyl) this includes, for example, methoxycarbonyloxy, ethoxycarbonyloxy, propoxycarbonyloxy, butoxycarbonyloxy, methoxyacetoxy, methoxypropanoyloxy, methoxybutanoyloxy, methoxy-pentanoyloxy, methoxyhexanoyloxy, ethoxyacetoxy, ethoxypropanoyloxy, ethoxybutanoyloxy, ethoxypentanoyloxy, ethoxyhexanoyloxy, propoxyacetoxy, propoxypropanoyloxy, propoxybutanoyloxy, and the like.

Aryl includes groups such as phenyl, naphthyl, thienyl or furyl group that is, as to each group, unsubstituted or monosubstituted with a hydroxyl, halo, $C_1$–$C_3$ alkyl, or $C_1$–$C_3$ alkoxy.

The term "halo" means chloro, fluoro, bromo or iodo.

When $R^5$ is an N-heterocyclic ring which optionally may have another hetero atom selected from N, O, or S in said ring, this includes pyrrolyidino, piperidino, hexamethyleneimino, piperazinyl, morpholinyl, thiomorphorpholinyl, 3-methylpyrroldinyl, 3-methylpiperidinyl, 4-hydroxy piperidinyl, 4-methylpiperazinyl, 4-ethyl piperazinyl, 2,3-dihydroindolyl, and 1,2,3,4-tetrahydroisoquinolyl. Generally, the heterocyclic group containing the nitrogen atom is a 5–6 membered ring.

Substituted $C_3$–$C_7$ cycloalkyl and substituted $C_3$–$C_7$ cycloalkenyl are those groups substituted with $C_1$–$C_6$ alkyl, hydroxyl, —O—C(O)$R^a$, wherein $R^a$ is as defined before, and/or an oxo group. Examples of such are 3-methylcycopentyl, 3-hydroxy cyclopentyl, 2-methylcyclohexyl, 3-methylcycohexyl, 4-methylcyclohexyl, 4-acetoxy cyclohexyl, 4-benzoyloxy cyclohexyl, 4-oxo cyclohexyl and 2-methyl cycloheptyl.

Specific examples of the compounds of the above-mentioned Formula I offered by the present invention include the following:

(6-hydroxy-2-cyclopentylbenzo[b]thien-3-yl)[4 -[2-[1-4-methylpiperazinyl)]ethoxy]phenyl]methanone,
(6-hydroxy-2-cyclohexylbenzo[b]thien-3-yl)[4-[2 -[1-(3-methylpyrrolidinyl)]ethoxy]phenyl]methanone,
(6-hydroxy-2-cyclohexylbenzo[b]thien-3-yl)[4-[2 -(N-thiomorpholinyl)ethoxy]phenyl]methanone,
(6-methanesulfonyloxy-2-cyclohexylbenzo[b]thien- 3-yl)[4-[2-(1-piperidinyl)ethoxy]phenyl]methanone,
(6-hydroxy-2-cycloheptylbenzo[b]thien-3-yl)[4 -[2-(N-morpholinyl)ethoxy]phenyl]methanone,
(6-hydroxy-2-cyclooctylbenzo[b]thien-3-yl)[4-[2 -(1-piperidinyl)ethoxy]phenyl]methanone,
(6-hydroxy-2-cyclododecylbenzo[b]thien-3-yl)[4 -[2-(1-pyrrolidinyl)ethoxy]phenyl]methanone,
[6-hydroxy-2-(2-methylcyclohexylbenzo[b]thien-3 -yl][4-[2-(dimethylamino)ethoxy]phenyl]methanone,
[6-hydroxy-2-(4-hydroxycyclohexyl)benzo[b]thien- 3-yl][4-[2-(1-pyrrolidinyl)ethoxy]phenyl]methanone,
[6-hydroxy-2-(4-hydroxycyclohexyl)benzo[b]thien- 3-yl][4-[2-(1-homopiperidinyl)ethoxy]phenyl]methanone,
(6-hydroxy-2-isopropylbenzo[b]thien-3-yl)[4-[2 -(diethylamino)ethoxy]phenyl]methanone,
(6-hydroxy-2-isopropylbenzo[b]thien-3-yl)[4-[2 -(1-homopiperidinyl)ethoxy]phenyl]methanone,
(6-hydroxy-2-sec-butylbenzo[b]thien-3-yl)[4-[2 -(1-piperidinyl)ethoxy]phenyl]methanone,
(6-hydroxy-2-cyclohexylbenzo[b]thien-3-yl)[4-[3 -(dimethylamino)propoxy]phenyl]methanone,
[6-hydroxy-2-(3-methylcyclohexyl)benzo[b]thien- 3-yl][4-[3-(1-piperidinyl)propoxy]phenyl]methanone,
(6-hydroxy-2-isopropylbenzo[b]thien-3-yl)[4-[3 -(1-piperidinyl)propoxy]phenyl]methanone,
(6-hydroxy-2-cyclohexylbenzo[b]thien-3-yl)[4-[2 -(Diethylcarbamoyl)ethyl]phenyl]methanone,
[6-hydroxy-2-(3-methylcyclohexyl)benzo[b]thien-3-yl][4-[2-(1-piperidinylcarbonyl)ethyl]phenyl]methanone,
(6-hydroxy-2-isopropylbenzo[b]thien-3-yl)[4-[2 -(1-piperidinylcarbonyl)ethyl]phenyl]methanone,
(6-hydroxy-2-cyclohexylbenzo[b]thien-3-yl)[4-[3 -(1-homopiperidinyl)propyl]phenyl]methanone,
(6-hydroxy-2-cyclohexylbenzo[b]thien-3-yl)[4-[3 -(N-morpholinyl)propyl]phenyl]methanone,
(6-hydroxy-2-isopropylbenzo[b]thien-3-yl)[4-[3 -(1-pyrrolidinyl)propyl]phenyl]methanone,
(6-hydroxy-2-cyclopentylbenzo[b]thien-3-yl)[4 -[3-(1-pyrrolidinylcarbonyl)propyl]phenyl]methanone,
[6-hydroxy-2-(2-methylcyclohexyl)benzo[b]thien-3-yl][4-[3-(1-piperidinylcarbonyl)propyl]phenyl]methanone,
(6-hydroxy-2-cyclopentylbenzo[b]thien-3-yl)[4 -[4-(1-piperidinyl)butyl]methanone, and
(6-hydroxy-2-isopropylbenzo[b]thien-3-yl[4-[4 -(1-pyrrolidinyl)butyl]phenyl]methanone.

The current invention concerns the discovery that the compounds of formula I are useful for lowering serum cholesterol levels. The methods of treatment provided by this invention are practiced by administering to a human in need of lower serum cholesterol levels a dose of a compound of formula I or a pharmaceutically acceptable salt or solvate thereof, that is effective to lower serum cholesterol levels. The present method includes both medical therapeutic and/ or prophylactic treatment, as appropriate. Generally, the compound is formulated with common excipients, diluents or carriers, and compressed into tablets, or formulated as elixirs or solutions for convenient oral administration, or administered by the intramuscular or intravenous routes. The compounds can be administered transdermally.

The compounds of formula I should lower serum cholesterol levels in humans. Excess serum cholesterol may result from a variety of conditions and disorders including a lack of endogenous estrogen such as occurs in women following cessation of menstruation due to natural, surgical, or other processes, and patients having gonadal dysgenesis.

The method also includes the administration of a compound of formula I and estrogen, either independently or in combination. The term estrogen as used herein refers to any compound which approximates the spectrum of activities of the naturally acting molecule which is commonly believed to be 17β-estradiol. Examples of such compounds include estriol, estrone, ethynyl estradiol, Premarin (a commercial preparation of conjugated estrogens isolated from natural sources—Ayerst), and the like.

All of the compounds used in the methods of the current invention can be made according to established or analogous procedures, such as those detailed in U.S. Pat. Nos. 4,133, 814, 4,418,068, and 4,380,635 all of which are incorporated by reference herein. Modifications to the above methods may be necessary to accommodate reactive functionalities of particular substituents. Such modifications would be both apparent to, and readily ascertained by, those skilled in the art.

With the present invention, the compound of the above-mentioned Formula I, or a salt thereof, can be manufactured, for example, by (a) allowing a compound expressed by the formula

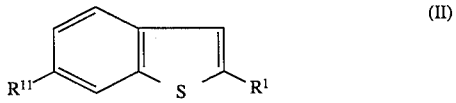

(II)

(where $R^{11}$ is a hydrogen atom or a lower alkyl group, and $R^1$ is defined the same as above)to react with a compound expressed by the formula

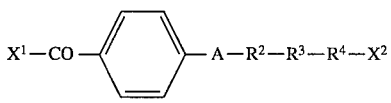

(III)

(Where $X^1$ and $X^2$ are each a halogen atom, and $R^2$, $R^3$ and $R^4$ are defined the same as above), and then allowing the compound thus obtained, which is expressed by the formula

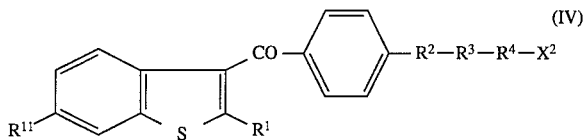

(IV)

(where $R^{11}$, $R^1$, $R^2$, $R^3$, $R^4$ and $X^2$ are defined the same as above), to react with a group represented by $R^5$ or (b) allowing the compound of the above-mentioned Formula II to react with a compound expressed by the formula

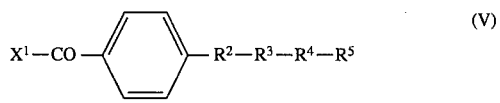

(V)

and then (c) converting the ring $R^{11}$ in the compound thus obtained, which is expressed by the formula

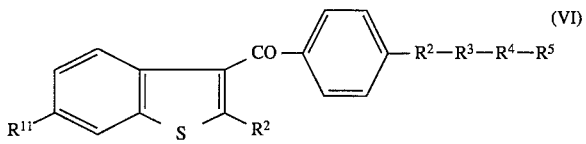

(VI)

as needed into a carbamoyloxy group that is unsubstituted or has been substituted with a hydroxy group, an acyloxy group, or an N,N-di-lower alkyl group, and then converting the compound thus obtained into a salt as needed.

The first step in the above method (a) is to allow the compound of the above Formula II to react with the compound from the above Formula III.

This reaction can be conducted according to a Friedel-Crafts acylation reaction, which is itself already known. In specific terms it can be conducted in an inert organic solvent (such as dichloromethane, 1,2-dichloroethane, chloroform, or another such halogenated hydrocarbon; benzene, chlorobenzene, or another such aromatic hydrocarbon; petroleum ether, hexane, or another such alkane; or nitrobenzene, nitromethane, or another such nitrohydrocarbon) and in the presence of a catalyst (such as aluminum chloride, aluminum bromide, zinc chloride, boron trifluoride, titanium tetrachloride, stannic chloride, or another such Lewis acid). The reaction temperature is generally from about room temperature to the reflux temperature of the reaction mixture, and a temperature ranging from room temperature to 100° C. is preferable.

As to the amount in which the compound from the above Formula III is used with respect to the compound from the above Formula II, using the compound from Formula III in a proportion of at least one mole, and preferably 1.1 to five moles, per mole of the compound from Formula II is advantageous.

As to the amount in which the catalyst is used, the catalyst usually should be used in a proportion of at least one mole, and preferably about 1.5 to 10 moles, per mole of the compound from the above Formula II.

This reaction produces the compound from the above Formula IV, and this compound is then allowed to react with the amine ($R^5$).

The reaction between the compound from the above Formula IV and the amine ($R^5$) generally can be conducted in the absence of a solvent or in an inert solvent (such as ethyl ether, tetrahydrofuran, dioxane, or another such ether; dimethylformamide, dimethylacetamide, or another such amide; benzene, toluene, or another such aromatic hydrocarbon; or dimethyl sulfoxide) The reaction temperature is usually between room temperature and the reflux temperature of the reaction mixture, and a range of 35° C. to the reflux temperature of the reaction mixture is preferable.

As to the amount in which the amine ($R^5$) is used with respect to the compound from the above Formula IV, using the amine ($R^5$) in an amount of one mole, and usually about 1.5 to 10 moles, per mole of the compound from Formula IV is favorable. When the reaction is conducted in the absence of a solvent, the amine ($R^5$) can be used in an excess amount and made to serve as a solvent as well.

It is preferable for the above reaction to be conducted in the presence of a deoxidant, such as pyridine, triethylamine, or another such organic base, or calcium carbonate, sodium carbonate, or another such inorganic base, but the amine is usually used in an excess amount and also made to serve as a deoxidant.

With the above method (b), the compound from the above Formula II is allowed to react with the compound from the above Formula VI.

The reaction can be conducted in the same manner as described for the reaction between the compound from the above Formula II and the compound from the above Formula III in the above method (a).

This produces a compound in which R in the compound from the above Formula I, which is the objective of the present invention, is a hydrogen atom or a lower alkyl group, i.e., the compound from the above Formula VI, and this compound can be converted as needed into the compound from the above Formula I in which R is a carbamoyloxy group that is unsubstituted or has been substituted with a hydroxy group, an acyloxy group, or an N,N-di-lower alkyl group.

The conversion to the compound from the above Formula I in which R is a hydroxy group can be accomplished by subjecting the compound from the above Formula VI in which $R^{11}$ is a lower alkyl group to a dealkylation reaction.

This dealkylation reaction generally can be conducted by treatment in an inert solvent (such as dichloromethane, chloroform, or another such halogen hydrocarbon; or benzene, toluene, or another such aromatic hydrocarbon), in the presence of both ethane thiol, dimethyl sulfide, or another such sulfur compound and aluminum chloride, boron trifluoride, or another such Lewis acid, and under heating preferably at the reflux temperature of the reaction mixture.

The conversion to the compound from the above Formula I in which R is an acyloxy group can be accomplished easily by acylating the compound from the above Formula I in which R is a hydroxy group by allowing it to react with an acyl halide in pyridine, for example, according to a known method.

The conversion to the compound from the above Formula I in which R is a carbamoyloxy group that is unsubstituted or has been substituted with an N,N-di-lower alkyl group can also be accomplished easily by allowing the compound from the above Formula I in which R is a hydroxy group to react with a substituted or unsubstituted carbamoyl chloride in pyridine, for example.

Of the compounds from the above Formula I of the present invention, a compound in which $R^4$ is —$CH_2$— can also be manufactured by another method, in which the compound expressed by the following formula

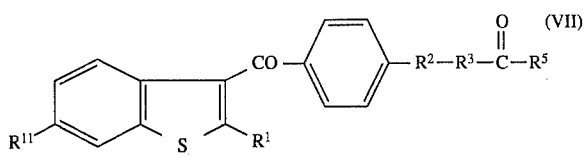

(VII)

The reduction of the compound from Formula VII can be accomplished, for example, by treatment with lithium aluminum hydride in tetrahydrofuran, dioxane, or another such solvent under heating and reflux. The oxidation of the compound thus obtained, which is expressed by the following formula

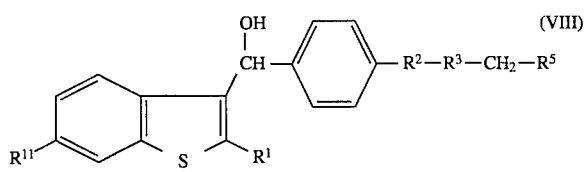

(VIII)

can be easily accomplished, for example, by treating this compound with chromium trioxide in pyridine.

When $R^1$ in the compound from the above Formula I of the present invention is a cycloalkyl group or cycloalkenyl group that has been substituted with a hydroxy group, it may be manufactured by subjecting the compound from Formula I in which $R^1$ is a cycloalkyl group or cycloalkenyl group that has been substituted with an oxo group to reduction with sodium borohydride or another such complex metal hydride in tetahydrofuran or another such solvent, for example.

The compound from Formula I in which $R^1$ is a cycloalkyl group or cycloalkenyl group that has been substituted with an acyloxy group can be manufactured by acylating according to a known method the compound from Formula I in which $R^1$ is a cycloalkenyl group chat has been substituted with a hydroxy group. In this reaction, when the compound from Formula I is one in which R is a hydroxy group R will also be acylated at the same time and converted into an acyloxy group.

The compound from the above Formula II, which is a starting material of the compound of the present invention, can be synthesized according to the following Reaction Formula 1.

Reaction Formula 1

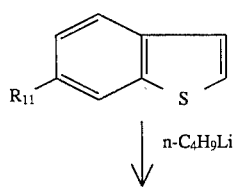

↓ n-C$_4$H$_9$Li

-continued
Reaction Formula 1

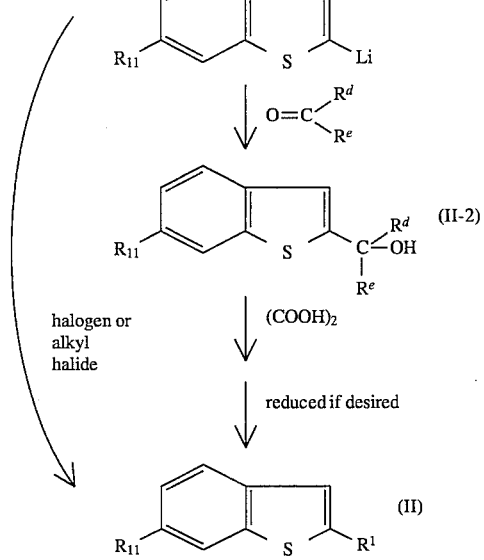

In the above formulas, $R^d$ and $R^e$ are each a lower alkyl group, or join together with the carbon atom to which they are bonded and form a cycloalkyl group that may be substituted with an oxo group or a lower alkyl group. $R^{11}$ is defined the same as above.

The compound from Formula II in which $R^d$ is a cycloalkyl group or cycloalkenyl group that has been substituted with a hydroxy group or an acyloxy group can be synthesized by converting a compound in which $R^1$ is a cycloalkyl group or cycloalkenyl group that has been substituted with an oxo group in the same manner as described for the conversion of $R^1$ in the compound from Formula I.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methane-sulfonate, naphthalene-1-sulfonate, naphthalene-2-sulfonate, p-toluenesulfonate, xylenesulfonate, tartarate, and the like.

In addition, some of the formula I compounds may form solvates with water or organic solvents such as ethanol. These solvates are also contemplated for use in the methods of this invention.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates and bicarbonates, as well as aliphatic and aromatic amines, aliphatic diamines and hydroxy alkylamines. Bases especially useful in the preparation of addition salts include ammonium hydroxide, potassium carbonate, sodium bicarbonate, calcium hydroxide, methylamine, diethylamine, ethylene diamine, cyclohexylamine and ethanolamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds either alone or in combination with estrogen can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agaragar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds either alone or in combination with estrogen can also be formulated as elixirs or solutions for convenient oral administration or as solutions appropriate for parenteral administration, for instance by intramuscular, subcutaneous or intravenous routes. Additionally, the compounds either alone or in combination with estrogen are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to lower serum cholesterol levels, according to this invention will depend upon the severity of the condition, the route of administration, and related factors that will be decided by the attending physician. Generally, accepted and effective daily doses will be from about 0.1 to about 1000 mg, and more typically from about 200 to about 600 mg. Such dosages will be administered to a subject in need of treatment from once to about three times each day, or more often as needed to effectively lower serum cholesterol levels. Generally, accepted and effective daily doses of estrogen will be from about 0.01 to about 4.0 mg, and more typically from about 0.1 to about 2.0 mg. Such doses are administered to a subject in need of treatment from once to about three times a day, or more often as needed.

The method of the present invention is useful in men, as well as women. The substantial absence of estrogenic response should allow men to employ the method of the present invention without evidencing the feminizing response of estrogen or estrogen agonists such as gynecomastia. Preferably, however, the method of the present invention is useful in women, more preferably estrogen deficient women. The estrogen deficiency could occur naturally, such as post-menopausal, or surgically. Patients undergoing or having undergone long-term administration of corticosteroids and those having gonadal dysgenesis may also employ the method of the present invention.

It is usually preferred to administer a compound of formula I in the form of an acid addition salt, as is customary in the administration of pharmaceuticals bearing a basic group, such as the piperidino ring. It is also advantageous to administer such a compound by the oral route to an aging human (e.g. a post-menopausal female). For such purposes the following oral dosage forms are available.

Formulations

In the formulations which follow, "Active ingredient" means a compound of formula I.

Formulation 1: Gelatin Capsules
Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

The components are blended and compressed to form tablets.

Alternatively, tablets each containing 0.1–1000 mg of active ingredient are made up as follows:

| Formulation 2: Tablets | |
| --- | --- |
| Ingredient | Quantity (mg/tablet) |
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 mL dose are made as follows:

| Formulation 3: Suspensions | |
|---|---|
| Ingredient | Quantity (mg/5 ml) |
| Active ingredient | 0.1–1000 mg |
| Sodium carboxymethyl cellulose | 50 mg |
| Syrup | 1.25 mg |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

The following nonlimiting test examples illustrate the methods of this invention.

Test Procedure

Seventy-five day old, female Sprague Dawley rats (weight range of 225 to 275 g: Charles River, Portage, Mich.) are used in this study. Ovariectomies are performed by the vendor. The animals are shipped one week post-surgery and housed in hanging wire cages. Room temperature is maintained at 22.2°±1.7° C. with a minimum relative humidity of 40%. The photoperiod in the room is 12 hr light and 12 hr dark, with light onset at 0600 hr. The animals have ad lib access to food (Teklad diet, TD 89222, 0.5% calcium, 0.4% phosphorus; Madison, Wis.) and water. The animals are allowed one week to acclimate to these conditions prior to experimental manipulation.

The compound is suspended in 20% β-cyclodextrin (CDX). 20% CDX is used as the control vehicle. 17α-Ethynyl-estradiol (obtained from Sigma Chemical Co.; St. Louis, Mo.) is dissolved in 20% CDX and is employed as an internal standard for these studies.

At the end of the one week acclimatization period (therefore, two weeks post-ovariectomy), dosing with test compounds is initiated. Oral gavages 20% CDX, the tested compound (0.1 to 10 mg/kg) or 17α-ethynyl-estradiol (100 µg/kg) are delivered daily for four consecutive days. On the evening following the final dose, the animals are fasted. The animals are anesthetized with a mixture of Ketaset® and Rompun® (67 and 6.7 mg/kg, respectively) the next morning and a 3 ml sample of blood is obtained by cardiac puncture. The animals are then asphyxiated with carbon dioxide and body weight and uterine weight are recorded. Uteri are then placed in a Tris buffer (pH=8.0) until analysis for eosinophil peroxidase (EPO) activity.

Uteri are kept at 4° C. until time of enzymatic analysis. The uteri are then homogenized in 50 volumes of 50 nM Tris buffer containing 0.005% Triton X-100. Upon addition of 0.01 hydrogen peroxide and 10 nM o-phenylenediamine (final concentration) in Tris buffer, increase in absorbance is monitored for one minute at 450 nm. The maximal velocity of a 15 second interval is determined over the initial, linear portion of the reaction curve.

Blood samples are allowed to clot at room temperature for 2 hr, and serum is obtained following centrifugation for 10 min. at 3000 rpm. Serum cholesterol is determined using a Boehringer Mannheim Diagnostics high performance cholesterol assay. Briefly, cholesterol esters are first hydrolyzed into free cholesterol and fatty acids by a microbial cholesterol esterase. The cholesterol is then oxidized to cholest-4-en-3-one and hydrogen peroxide. The hydrogen peroxide is then reacted with phenol and 4-aminophenazone in the presence of peroxidase to produce a p-quinone imine dye, which is read spectrophotometrically at 500 nm. Cholesterol concentration is then calculated against a standard curve.

Experimental groups consist of 5 animals. Data for control and treated rats are compared by one way analysis of variance (ANOVA). When statistical significance is indicated ($p<0.05$) post-hoc range testing is performed (Fishers PLSD test).

INFLUENCE OF COMPOUNDS ON SERUM CHOLESTEROL

In summary, ovariectomy of the rats causes an increase in serum cholesterol as compared to intact vehicle treated controls. Estrogen, administered in the orally active form of ethynyl estradiol ($EE_2$), causes a decrease in serum cholesterol in a dose dependent manner, but it also exerts a stimulatory action on the uterus resulting in uterine weights approaching that of an intact rat.

In the above assay, the compounds of the invention cause a serum cholesterol decrease in a dose dependent manner.

EXAMPLE 1

1 mL of pyrrolidine is added to 30 mg of (6-methoxy-2-cyclopentylbenzo[b]thien-3-yl)[4-(2-chloroethoxy)phenyl]methanone, and this mixture is heated and refluxed for one hour. The mixture is condensed under reduced pressure to distill off the pyrrolidine, and then is refined by TLC (developing solvent was chloroform:methanol=19:1) which gives 28 mg of (6-methoxy-2-cyclopentylbenzo[b]thien-3-yl)[4-[2-(1-pyrrolidinyl)ethoxy)phenyl]methanone.

1H-NMR (CDCL3,δ): 0.94–2.47 (12H,m), 2.55–2.79 (4H,m), 2.94 (2H,t, J=6 Hz), 3.41 (1H, m), 3.84 (3H,s), 4.19 (2H, t, J=6 Hz ), 6.69–7.87 (7H,m).

MS(m/z): 449(M+), 84.

The following listed compounds may be synthesized in the same manner as in Example 1.

(6-methoxy-2-cyclopentylbenzo[b]thien-3-yl)[4-[2-(1-homopiperidinyl)]ethoxy]phenyl]methanone (6-methoxy-2-cyclopentylbenzo[b]thien-3-yl)[4-[2-[1-3-methylpiperidinyl)]ethoxy'phenyl]methanone (6-methoxy-2-cyclohexylbenzo[b]thien-3-yl)[4-[2-[1-(4-methylpiperidinyl)]ethoxy]phenyl]methanone (6-methoxy-2-cyclohexylbenzo[b]thien-3-yl)[4-[2-(1,2,3,4-tetrahydroisoquinolinyl)]ethoxy]phenyl]methanone (6-methoxy-2-cyclohexylbenzo[b]thien-3-yl[4-[2-[1-(4-hydroxypiperidinyl)]ethoxy]phenyl]methanone (6-methoxy-2-cyclohexylbenzo[b]thien-3-yl)[4-[2-(diethylamino)ethoxy]phenyl]methanone (6-methoxy-2-cycloheptylbenzo[b]thien-3yl)[4-[2-(1-pyrrolidinyl)ethoxy]phenyl]methanone (6-methoxy-2-cycloheptylbenzo[b]thien-3-yl)[4-[2-(1-homopiperidinyl)ethoxy]phenyl]methanone (6-methoxy-2-cycloheptylbenzo[b]thien-3-yl)[4-[2-[1 -(3-methylpiperidinyl)]ethoxy]phenyl]methanone (6-methoxy-2-(2-methylcyclohexyl)benzo[b]thien-3 -yl][4-[2-(1-pyrrolidinyl)ethoxy]phenyl]methanone

[6-methoxy-2-(2-methylcyclohexyl)benzo[b]thien-3 -yl][4-[2-(1-piperidinyl)ethoxy]phenyl]methanone

[6-methoxy-2-(2-methylcyclohexyl)benzo[b]thien-3 -yl][4-[2-(1-homopiperidinyl)ethoxy]phenyl]methanone

[6-methoxy-2-(3-methylcyclohexyl)benzo[b]thien-3 -yl][4-[2-(1-pyrrolidinyl)ethoxy]phenyl]methanone 6-methoxy-2-(3-methylcyclohexyl)benzo[b]thien-3 -yl][4-[2-(1-piperidinyl)ethoxy]phenyl]methanone

[6-methoxy-2-(3-methylcyclohexyl)benzo[b]thien-3 -yl][4-[2-(1-homopiperidinyl)ethoxy]phenyl]methanone

[6-methoxy-2-(3-methylcyclohexyl)benzo[b]thien-3 -yl][4-[2-[1-(3-methylpiperidinyl)ethoxy]phenyl]methanone (6-methoxy-2-cyclopentylbenzo[b]thien-3-yl)[4-[3-(1 -piperidinyl)propoxy]phenyl]methanone (6-methoxy-2-cyclohexylbenzo[b]thien-3-yl)[4-[3 -(diethylamino)propoxy]phenyl]methanone (6-methoxy-2-cyclohexylbenzo[b]thien-3-yl)[4-[3-(1 -pyrrolidinyl)propoxy]phenyl]methanone (6-methoxy-2-cyclohexylbenzo[b]thien-3-yl)[4-[3-(1 -piperidinyl)propoxy]phenyl]methanone (6-methoxy-2-cyclohexylbenzo[b]thien-3-yl)[4-[3-(1 -homopiperidinyl)propoxy]phenyl]methanone (6-methoxy-2-cyclohexylbenzo[b]thien-3-yl)[4-[3-[1-(3 -methylpiperidinyl)]propoxy]phenyl]methanone (6-methoxy-2-cyclohexylbenzo[b]thien-3-yl)[4-[3-[1-(4 -methylpiperazin)]propoxy]phenyl]methanone (6-methoxy-2-cyclohexylbenzo[b]thien-3-yl)[4-[3-[2 -(1,2,3,4-tetrahydroisoquinolinyl)]propoxy]phenyl]methanone (6-methoxy-2-cycloheptylbenzo[b]thien-3-yl)[4-[3-(1 -pyrrolidinyl)propoxy]phenyl]methanone (6-methoxy-2-cycloheptylbenzo[b]thien-3-yl)[4-[3-(1 -piperidinyl)propoxy]phenyl]methanone (6-methoxy-2-cycloheptylbenzo[b]thien-3-yl)[4-[3-(1 -homopiperidinyl)propoxy]phenyl]methanone (6-methoxy-2-cyclododecylbenzo[b]thien-3-yl)[4-[2-(1 -piperidinyl)ethoxy]phenyl]methanone (6-methoxy-2-isopropylbenzo[b]thien-3-yl)[4-[2-(1 -piperidinyl)ethoxy]phenyl]methanone (6-methoxy-2-isopropylbenzo[b]thien-3-yl)[4-[2-(1 -piperidinyl)ethoxy]phenyl]methanone

EXAMPLE 2

49 mg of sodium hydride is added to a THF solution of 0.2 mL of pyrrolidine, and this mixture is agitated for one hour at room temperature. To this is added 54 mg of (6 -methoxy-2-cyclohexylbenzo[b]thien-3-yl)[4-(2 -chloroethoxy)phenyl]methanone, and this mixture is heated and refluxed for ten hours. Water is added and extracted with ethyl acetate, and this extract is refined by TLC (developing solvent was chloroform:methanol=19:1), which gives 12 mg of (6-methoxy-2-cyclohexylbenzo[b]thien-3 -yl)[4-[2-(1-pyrrolidinyl)ethoxy)phenyl]methanone.

$^1$H-NMR(CDCL$_3$, δ): 1.15–2.10 (14H, m), 2.67–2.86 (4H, m), 3.00 (2H, t, J=5.7 Hz), 3.4 (1H, m), 3.84 (3H, s), 4.23(2H, t, J=5.7 Hz), 6.78–7.86 (7H, m).

MS(m/z): 463(M$^+$), 84.

The following compounds may be synthesized in the same manner as in Example 2.

(6-methoxy-2-cyclohexylbenzo[b]thien-3-yl)[4-[2-(1 -homopiperidinyl)ethoxy]phenyl]methanone (6-methoxy-2-cyclohexylbenzo[b]thien-3-yl)[4-[2-(N-morpholinyl)ethoxy]phenyl]methanone

EXAMPLE 3

50 mg of (6-methoxy-2-cyclohexylbenzo[b]thien-3-yl)[4 -(2-chloroethoxy)phenyl]methanone is dissolved in 5 mL of DMF, 20 mg of potassium iodide and 0.5 mL of 3 -methylpiperidine are added, and this mixture is agitated for eight hours at approximately 40° C., for two days at room temperature, and for two hours at approximately 50° C. The reaction mixture is condensed underreduced pressure, a saturated aqueous solution of sodium hydrogencarbonate is added, and an extraction is performed with ethyl acetate. The organic layer is washed with saturated salt water, after which it is dried with anhydrous magnesium sulfate. The solvent is distilled off, and the residue is refined by TLC (developing solvent: chloroform), which gives 31 mg of (6-methoxy-2-cyclohexylbenzo[b]thien-3-yl)[4-[2-[1-(3 -methylpiperidinyl)]ethoxy]phenyl]methanone.

1H-NMR(CKCL3,): 0.87 (3H, d, J=5.7 Hz), 1.01–2.76 (17H, m), 2.73–3.11(5H, m), 3.84 (3H, s), 4.18 (2H, t, J=6 Hz), 6.75–7.88 (7H, m).

MS (m/z): 491 (M$^+$), 112.

The following compounds may be synthesized in the same manner as in Example 3.

(6-methoxy-2-cyclohexylbenzo[b]thien-3-yl)]4-[3-(N-morpholinyl)propoxy]phenyl]methanone

EXAMPLE 4

88 mg of chromium trioxide is added to 5 mL of pyridine to produce a yellow solution with the consistency of gruel, to which is added a pyridine solution of 105 mg of (6-methoxy-2-cyclohexylbenzo[b]thien-3-yl)[4-[3-(1 -poperidinyl)propyl]phenyl]methanol, and this mixture is agitated for one hour at room temperature. Ice is put into the reaction mixture, after the organic layer is extracted with ethyl acetate and then dried with anhydrous magnesium sulfate. The solvent is distilled off, and the crude product thus obtained is refined by TLC (developing solvent was chloroform:methanol=19:1), which gives 47 mg of (6 -methoxy-2-cyclopentylbenzo[b]thien-3-yl)[4-[3-(1 -piperidinyl)propyl]phenyl]methanone.

$^1$H-NMR(CDCl$_3$, δ): 1.15–2.09 (16H,m), 2.30–2.57 (6H, m), 2.62–2.96 (4H,m), 3.84 (3H, s), 6.78–7.79 (7H,m).

MS (m/z): 475 (M$^+$), 98.

The following compounds may be synthesized in the same manner as in Example 4.

(6-methoxy-2-cycloheptylbenzo[b]thien-3-yl)[4-[3-(1 -piperidinyl)propyl]phenyl]methanone (6-methoxy-2-cyclohexylbenzo[b]thien-3-yl)[4-[3 -(dimethylamino)propyl]phenyl]methanone (6-methoxy-2-cyclohexylbenzo[b]thien-3-yl)[4-[3-(1 -pyrrolidinyl)propyl]phenyl]methanone (6-methoxy-2-cylohexylbenzo[b]thien-3-yl)[4-[4-(1 -pyrrolidinyl)butyl]phenyl]methanone

EXAMPLE 5

50 mg of (6-methoxy-2-(4-oxocyclohexyl)benzo[b]thien-3-yl][4-[2-(1-piperidinyl)ethoxy]phenyl]methanone is dissolved in 4 mL of methanol and 0.5 mL of THF and cooled with ice. 6 mg of sodium borohydride is added, and this mixture is agitated at 0° C. for 15 minutes. Water is added to the reaction mixture, and the organic layer is extracted with ethyl acetate, then washed with water and dried with anhydrous sodium sulfate, after which the solvent is distilled off. The crude product thus obtained is refined by TLC (developing solvent was chloroform:methanol=19:1), which gives 32 mg of [6-methoxy-2-(4-hydroxycyclohexyl)benzo[b]thien-3-yl)[4-[2-(1-piperidinyl)ethoxy]phenyl]methanone.

¹H-NMR(CDCL3): 1.10–2.20(14H,m), 2.60–3.00 (4H, m), 3.06(2H,t, J=6 Hz), 3.60 (2H,m), 3.85 (3H, s), 4.41 (2H, t, J=6 Hz), 6.70–7.30 (5H,m), 7.80(2H, d,J=9 HZ).

MS(m/z): 493(M⁺), 382, 323, 98.

EXAMPLE 6

200 mg of aluminum chloride is added to 20 mL of dichloromethane, and while this mixture is being agitated at 0° C., 10 mL of a dichloromethane solution of 0.3 mL of oxalyl chloride is added dripwise and agitated for ten minutes at 0° C. 2 mL of a dichloromethane solution of 100 mg of 4-phenylbutylpyrrolidine is added dropwise and agitated for 30 minutes at room temperature. Water is added, and the organic layer is extracted with dichloromethane and dried with anhydrous magnesium sulfate, after which it is condensed. The residue is dissolved in 20 mL of dichloromethane, 100 mg of 6-methoxy-2-cyclohexylbenzo[b]thiophene and 200 mg of aluminum chloride are added, and this mixture is agitated for two hours at room temperature. 1 mL of THF, 0.3 mL of 20% hydrochloric acid, and 1 mL of water are added to the reaction mixture at 25° C. or below, after which a saturated aqueous solution of sodium hydrogencarbonate is added to render the solution alkaline, and the organic layer is extracted with dichloromethane and dried with anhydrous magnesium sulfate. The solvent is distilled off, and the crude product thus obtained is refined by TLC (developing solvent was chloroform: n-hexane= 1:5), which gives 54 mg of (6-methoxy-2-cyclohexylbenzo[b]thien-3-yl)[4-[3-(1-pyrrolidinylcarbonyl)propyl]phenyl]methanone.

MS(m/z): 489(M⁺), 113.

The following compounds may be synthesized in the same manner as in Example 6.
(6-methoxy-2-cyclohexylbenzo[b]thien-3-yl)[4-[3-(1-piperidinylcarbonyl)propyl]phenyl]methanone
(6-methoxy-2-cyclohexylbenzo[b]thien-3-yl)[4-[4-(1-piperidinyl)butyl]phenyl]methanone
(6-methoxy-2-cyclohexylbenzo[b]thien-3-yl)[4-[3-(dimethylcarbamoyl)propyl]phenyl]methanone

EXAMPLE 7

35 mg of (6-methoxy-2-cyclopentylbenzo[b]thien-3-yl) [4-[2-(dimethylamino)ethoxy]phenyl]methanone is dissolved in 5 mL of dichloromethane, 65 mg of aluminum chloride and 0.03 mL of ethanethiol are added, and this mixture is agitated for two hours at room temperature. 0.3 mL of THF, 0.075 mL of 20% hydrochloric acid, and 0.3 mL of water are added to the reaction mixture, after which a saturated aqueous solution of sodium hydrogencarbonate is added to render the solution alkaline, and the organic layer is extracted with ethyl acetate and dried with anhydrous magnesium sulfate. The solvent is distilled off, and the crude product thus obtained is refined by TLC (developing solvent was chloroform:methanol=19:1), which gives 21 mg of (6-hydroxy-2-cyclopentylbenzo[b]thien-3-yl)[4-[2-(dimethylamino)ethoxy]phenyl]methanone.

¹H-NMR(CD₃OD, δ): 1.24–2,27(8H,m), 2.37(6H, s), 2,81 (2H, t,J=5.5 Hz), 4.18(2H, t, J=5.5 Hz), 6.68–7.87(7H, m).

MS (m/z): 409 (M⁺), 58.

The following compounds may be synthesized in the same manner as in Example 7.
(6-hydroxy-2-cyclopentylbenzo[b]thien-3-yl)[4-[2-(diethylamino)ethoxy]phenyl]methanone
(6-hydroxy-2-cyclopentylbenzo[b]thien-3-yl)[4-[2-(1-pyrrolidinyl)ethoxy]phenyl]methanone
(6-hydroxy-2-cyclopentylbenzo[b]thien-3-yl)[4-[2-(1-homopiperidinyl)ethoxy]phenyl]methanone
(6-hydroxy-2-cyclopentylbenzo[b]thien-3-yl)[4-[2-[1-(3-methylpiperidinyl)]ethoxy]phenyl]methanone
(6-hydroxy-2-cyclohexylbenzo[b]thien-3-yl)[4-[2-(dimethylamino)ethoxy]phenyl]methanone
(6-hydroxy-2-cyclohexylbenzo[b]thien-3-yl)[4-[2-(diethylamino)ethoxy]phenyl]methanone
(6-hydroxy-2-cyclohexylbenzo[b]thien-3-yl)[4-[2-(1-pyrrolindinyl)ethoxy]phenyl]methanone
(6-hydroxy-2-cyclohexylbenzo[b]thien-3-yl)[4-[2-(1-piperidinyl)ethoxy]phenyl]methanone
(6-hydroxy-2-cyclohexylbenzo[b]thien-3-yl)[4-[2-(1-homopiperidinyl)ethoxy]phenyl]methanone
(6-hydroxy-2-cyclohexylbenzo[b]thien-3-yl)[4-[2-[1-(3-methylpiperidinyl)]ethoxy]phenyl[methanone
(6-hydroxy-2-cyclohexylbenzo[b]thien-3-yl)[4-[2-(N-morpholinyl)ethoxy]phenyl]methanone
(6-hydroxy-2-cyclohexylbenzo[b]thien-3-yl)[4-[1-(4-methylpiperazinyl)]ethoxy]phenyl]methanone
(6-hydroxy-2-cyclohexylbenzo[b]thien-3-yl)[4-[20[2-(1,2,3,4-tetrahydroisoquinolinyl)]ethoxy]phenyl]methanone
(6-hydroxy-2-cyclohexylbenzo[b]thien-3-yl)[4-[2-[1-(4-hydroxypeperidinyl)]ethoxy]phenyl]methanone
(6-hydroxy-2-cycloheptylbenzo[b]thien-3-yl)[4-[2-(dimethylamino)ethoxy]phenyl]methanone
(6-hydroxy-2-cycloheptylbenzo[b]thien-3-yl)[4-[2-(dimethylamino)ethoxy]phenyl]methanone
(6-hydroxy-2-cycloheptylbenzo[b]thien-3-yl)[4-[2-1-pyrrolidinyl)ethoxy]phenyl]methanone
(6-hydroxy-2-cycloheptylbenzo[b]thien-3-yl)[4-[2-1-piperidinyl)ethoxy]phenyl]methanone
(6-hydroxy-2-cycloheptylbenzo[b]thien-3-yl)[4-[2-1-homopiperidinyl)ethoxy]phenyl]methanone
(6-hydroxy-2-cyclohexylbenzo[b]thien-3-yl)[4-[2-[1-(3-methylpiperidinyl)]ethoxy]phenyl]methanone
[6-hydroxy-2-(2-methylcyclohexyl)benzo[b]thien-3-yl][4-[2-(1-pyrrolidinyl)ethoxy]phenyl]methanone
[6-hydroxy-2-(2-methylcyclohexyl)benzo[b]thien-3-yl][4-[2-(1-piperidinyl)ethoxy]phenyl]methanone
[6-hydroxy-2-(2-methylcyclohexyl)benzo[b]thien-3-yl][4-[2-(1-homopiperidinyl)ethoxy]phenyl]methanone
[6-hydroxy-1-(3-methylcyclohexyl)benzo[b]thien-3-yl][4-[2-(dimethylamino)ethoxy]phenyl]methanone
[6-hydroxy-2-(3-methylcyclohexyl)benzo[b]thien-3-yl][4-[2-(diethylamino)ethoxy]phenyl]methanone
[6-hydroxy-2-(3-methylcyclohexyl)benzo[b]thien-3-yl][4-[2-(1-pyrrolidinyl)ethoxy]phenyl]methanone
[6-hydroxy-2-)3-methylcyclohexyl)benzo[b]thien-3-yl][4-[2-(1-piperidinyl)ethoxy]phenyl]methanone
[6-hydroxy-2-(3-methylcyclohexyl)benzo[b]thien-3-yl][4-[2-(1-homopiperidinyl)ethoxy]phenyl]methanone
[6-hydroxy-2-(3-methylcyclohexyl)benzo[b]thien-3-yl][4-[2-(3-methylpiperidinyl)ethoxy]phenyl]methanone
[6-hydroxy-2-(4-methylcyclohexyl)benzo[b]thien-3-yl][4-[2-(1-piperidinyl)ethoxy]phenyl]methanone
[6-hydroxy-2-(1-methylcyclooctenyl)benzo[b]thien-3-yl][4-[2-(1-piperidinyl)ethoxy]phenyl]methanone
(6-hydroxy-2-methylbenzo[b]thien-3yl)[4-[2-(1-pyrrolidinyl)ethoxy]phenyl]methanone
(6-hydroxy-2-cyclopentylbenzo[b]thien-3-yl)[4-[3-(1-piperidinyl)propoxy]phenyl]methanone (6-hydroxy-2-cyclohexylbenzo[b]thien-3-yl)[4-[3 -(diethylamino)propoxy]phenyl]methanone
(6-hydroxy-2-cyclohexylbenao[b]thien-3-yl)[4-[3-(1 -pyrrolidinyl)propoxy]phenyl]methanone
(6-hydroxy-2-cyclohexylbenzo[b]thien-3-yl)[4-[3-(1 -piperidinyl)propoxy]phenyl]methanone
(6-hydroxy-2-cyclohexylbenzo[b]thien-3-yl)[4-[3-(1 -homopiperidinyl)propoxy]phenyl]methanone
(6-hydroxy-2-cyclohexylbenzo[b]thien-3-yl)[4-[3-[1-(3 -methylpiperidinyl)])propoxy]methanone
(6-hydroxy-2-cyclohexylbenzo[b]thien-3-yl)[4-[3-(N-morpholinyl)propoxy]phenyl]methanone
(6-hydroxy-2-cyclohexylbenzo[b]thien-3-yl)[4-[3-[1-(4 -methylpiperazinyl]propoxy]phenyl]methanone
(6-hydroxy-2-cyclohexylbenzo[b]thien-3-yl)[4-[3-[2 -(1,2, 3,4-tetrahydroisoquinolinyl)]propoxy]phenyl]methanone
(6-hydroxy-2-cycloheptylbenzo[b]thien-3-yl)[4-[3-(1 -pyrrolidinyl)propoxy]phenyl]methanone
(6-hydroxy-2-cycloheptylbenzo[b]thien-3-yl)[4-[3-(1 -piperidinyl)propoxy]phenyl]methanone
(6-hydroxy-2-cycloheptylbenzo[b]thien-3-yl)[4-[3-(1 -homopiperidinyl)propoxy]phenyl]methanone
(6-hydroxy-2-cyclohexylbenzo[b]thien-3-yl)[4-[2-(1 -piperidinylcarbonyl)ethyl]phenyl]methanone
(6-hydroxy-2-cyclohexylbenzo[b]thien-3-yl)[4-[3-(1 -piperidinyl)propyl]phenyl]methanone
(6-hydroxy-2-cycloheptylbenzo[b]thien-3-yl)[4-[2-(1 -piperidinylcarbonyl)ethyl]phenyl]methanone
(6-hydroxy-2-cycloheptylbenzo[b]thien-3-yl)[4-[3-)1 -piperidinyl)propyl]phenyl]methanone
(6-hydroxy-2-cyclohexylbenzo[b]thien-3-yl)[4-[3 -(dimethylamino)propyl]phenyl]methanone
(6-hydroxy-2-cyclopentylbenzo[b]thien-3-yl)[4-[2-(1 -piperidinylcarbonyl)ethoxy]phenyl]methanone
[6-hydroxy-2-(4-hydroxycyclohexyl)benzo[b]thien-3 -yl][4-[2-(1-piperidinyl)ethoxy]phenyl]methanone
(6-hydroxy-2-cyclododecylbenzo[b]thien-3-yl)[4-[2-(1 -piperidinyl)ethoxy]phenyl]methanone
(6-hydroxy-2-isopropylbenzo[b]thien-3-yl)[4-[2-(1 -piperidinyl)ethoxy]phenyl]methanone
(6-hydroxy-2-isopropylbenzo[b]thien-3-yl)[4-[2-(1 -pyrrolidinyl)ethoxy]phenyl]methanone
(6-hydroxy-2-cyclohexylbenzo[b]thien-3-yl)[4-[2-(1 -pyrrolidinylcarbonyl)ethyl]phenyl]methanone
(6-hydroxy-2-cyclohexylbenzo[b]thien-3-yl)[4-[3-(1 -pyrrolidinyl)propyl]phenyl]methanone
[6-hydroxy-2-(2-methylcyclohexyl)benzo[b]thien-3 -yl][4-[2-)1-pyrrolidinylcarbonyl)ethyl]phenyl]methanone
(6-hydroxy-2-cycloheptylbenzo[b]thien-3-yl)[4-[2-(1 -pyrrolidinylcarbonyl)ethyl]phenyl]methanone
(6-hydroxy-2-cyclohexylbenzo[b]thien-3-yl)[4-[3-(1 -pyrrolidinyl)propyl]phenyl]methanone
(6-hydroxy-2-cyclohexylbenzo[b]thien-3-yl)[4-[4-(1 -pyrrolidinyl)butyl]phenyl]methanone
(6-hydroxy-2-cyclohexylbenzo[b]thien-3-yl_[4-[3-(1 -piperidinylcarbonyl)propyl]phenyl]methanone
(6-hydroxy-2-cyclohexylbenzo[b]thien-3-yl)[4-[4-(1 -piperidinyl)butyl]phenyl]methanone

EXAMPLE 8

27 mg of (6-hydroxy-2-cyclohexylbenzo[b]thien-3yl)[4 -[2-(1-piperidinyl)ethoxy]phenyl]methanone is dissolved in 1 mL of pyridine, 0.1 mL of benzoyl chloride is added, and this mixture is agitated for one hour at room temperature. Ice is added to the reaction mixture, and the system is agitated for one hour. The organic layer is extracted with ethyl acetate and dried with anhydrous magnesium sulfate. The solvent is distilled off, and the crude product thus obtained is refined by TLC (developing solvent was chloroform:methanol=9:1), which gives 37 mg of(6 -benzoyloxy-2-cyclohexylbenzo[b]thien-3-yl)[4-[2-(1 -piperidinyl)ethoxy]phenyl]methanone.

$^1$H-NMR(CD$_3$OD, δ): 1.17–1.96(16H,m), 2.62–2.73(4H, m), 2.92 (2H, t, J=5.6 Hz), 4.25 (2H, t,J=5.6 Hz), 6.98–8.22 (12H,m).

MS (m/z): 567 (M$^+$), 98.

The following compounds may be synthesized in the same manner as in Example 8.
(6-dimethylcarbamoyloxy-2-cyclohexylbenzo[b]thien-3 -yl)[4-[2-(1-piperidinyl)ethoxy]phenyl]methanone
(6-benzoyloxy-2-cyclohexylbenzo[b]thien-3-yl)[4-[2-(1 -pyrrolidinyl)ethoxy]phenyl]methanone
(6-benzoyloxy-2-cycloheptylbenzo[b]thien-3-yl)[4-[3 -)1-piperidinyl)propoxy]phenyl]methanone
(6-benzoyloxy-2-cycloheptylbenzo[b]thien-3-yl)[4-[3 -(1-homopiperidinyl)propoxy]phenyl]methanone
(6-benzoyloxy-2-cycloheptylbenzo[b]thien-3-yl)[4-[3 -(1-pyrrolidinyl)propoxy]phenyl]methanone

EXAMPLE 9

A mixture of 10 mg of (6-hydroxy-2-(4 -hydroxycyclohexyl)benzo[b]thien-3-yl)[4-[2-(1 -piperidinyl)ethoxy]phenyl]methanone, 0.5 mL of acetic anhydride, and 0.5 mL of pyridine is agitated for 18 hours at room temperature. Ice is added to the reaction mixture, and the system is agitated for 30 minutes, after which the organic layer is extracted with ethyl acetate, washed with water and a saturated aqueous solution of sodium hydrogencarbonate, and dried with anhydrous magnesium sulfate. The solvent is distilled off, and the crude product thus obtained is refined by TLC (developing solvent was chloroform:methanol=9:1), which gives 5 mg of [6 -acetoxy-2-(4-acetoxycyclohexyl)benzo[b]thien-3-yl][4-[2-(1 -piperidinyl)ethoxy]phenyl]methanone.

1H=NMR(CDCL3,): 1.10–2.20(14H,m), 2.01(3H, s), 2.31(3H,2), 2.60–2.90(4H,m), 3.03(2 H, t, J=6 Hz), 4.36(2H, t, J=6 Hz), 4.70 (1H, m), 6.80–7.60 (5 h, m), 7.80 (2H, d, J+8.8 Hz).

MS(m/z): 563(M+), 452, 434, 393, 351, 309, 98.

The following compound may be synthesized in the same manner as in Example 9.
(6-acetoxy-2-cyclohexylbenzo[b]thien-3-yl)[4-[2-(1 -piperidinyl)ethoxy]phenyl]methanone

We claim:

1. A method of lowering serum cholesterol levels comprising administering to a human in need of treatment a serum cholesterol lowering amount of a compound having the formula

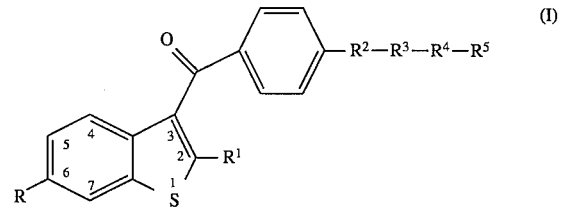

wherein R is hydrogen; hydroxy; $C_1$–$C_6$ alkoxy; a group of the formula —O—C(O)—R$^a$, wherein R$^a$ is hydrogen, $C_1$–$C_6$ alkyl optionally substituted with amino optionally substituted once or twice with $C_1$–$C_6$ alkyl, halo, carbonyl, $C_1$–$C_6$ alkoxycarbonyl, $C_1$–$C_7$ alkanoyloxy, carbamoyl and/or aryl; or $R^a$ is $C_1$–$C_6$ alkenyl optionally substituted with aryl; or $R^a$ is a $C_3$–$C_7$ cycloalkyl; or $R^a$ is aryl optionally substituted with hydroxy, $C_1$–$C_6$ alkyl, $C_1$–$C_6$ alkoxy, and/or halo; or $R^a$ is —O—aryl, said aryl optionally substituted with hydroxy $C_1$–$C_6$ alkyl, $C_1$–$C_6$ alkoxy, and/or halo, or R is a group of the formula —O—$SO_2$—$R^b$ wherein $R^b$ may be $C_1$–$C_6$ alkyl or aryl optionally substituted with $C_1$–$C_6$ alkyl;

or R is carbamoyloxy wherein the nitrogen may be substituted once or twice with $C_1$–$C_6$ alkyl;

or R is a group of the formula —O—C(O)$R^c$—O—($C_1$–$C_6$ alkyl) wherein $R^c$ is a bond or $C_1$–$C_6$ alkanediyl;

$R^1$ is halo, $C_1$–$C_6$ alkyl, $C_1$–$C_7$ alkyl substituted with $C_1$–$C_6$ alkyl, substituted or unsubstituted $C_3$–$C_7$ cycloalkyl, or substituted or unsubstituted $C_3$–$C_7$ cycloalkenyl;

$R^2$ is O or $CH_2$;

$R^3$ is $CH_2$ or $(CH_2)_2$;

$R^4$ is

$CH_2$, or a bond; and $R^5$ is amino, or a pharmaceutically acceptable salt or solvate thereof.

2. A method of claim 1 wherein the human is a female.

3. A method of claim 2 wherein the female is estrogen deficient.

4. A method of claim 3 wherein the female is post-menopausal.

5. A method according to claim 1 wherein $R^1$ is a group having the formula $$-\underset{(C_1-C_6\,\text{alkyl})}{\overset{}{\underset{|}{C}}}-(C_1-C_6\,\text{alkyl})$$

or a cycloalkyl group with a carbon number of three to seven that may be substituted with $C_1$–$C_6$ alkyl or hydroxy.

6. A method of claim 5 wherein R is hydroxy.

7. A method according to claim 6 wherein $R^2$ is O and $R^4$ is $CH_2$.

8. The method according to claim 6 wherein $R^2$ is $CH_2$.

9. The method according to claim 5 wherein R is $C_1$–$C_6$ alkoxy.

* * * * *

UNITED STATES PATENT AND TRADEMARK OFFICE
CERTIFICATE OF CORRECTION

PATENT NO. : 5,552,433

DATED : September 3, 1996

INVENTOR(S) : Henry U. Bryant and Timothy A. Grese

It is certified that error appears in the above-indentified patent and that said Letters Patent is hereby corrected as shown below:

Column 22, line 3, delete "$R^5$ is amino," and insert -- $R^5$ is amino optionally substituted once or twice with $C_1-C_6$ alkyl, --.

Signed and Sealed this

Twenty-first Day of January, 1997

Attest:

BRUCE LEHMAN

Attesting Officer

Commissioner of Patents and Trademarks